United States Patent [19]

Ball et al.

[11] Patent Number: 5,187,233

[45] Date of Patent: Feb. 16, 1993

[54] PROCESS FOR EMULSION POLYMERIZATION OF GRAFT COPOLYMERS

[75] Inventors: Peter Ball, Emmerting; Josef Christ, Burghausen; Albin Frank, Burghausen; Klaus Marquardt, Burghausen; Manfred Selig, Burghausen, all of Fed. Rep. of Germany

[73] Assignee: Wacker-Chemie GmbH, Munich, Fed. Rep. of Germany

[21] Appl. No.: 490,729

[22] Filed: Mar. 8, 1990

Related U.S. Application Data

[63] Continuation-in-part of Ser. No. 254,368, Oct. 5, 1988, abandoned.

[30] Foreign Application Priority Data

Dec. 18, 1987 [DE] Fed. Rep. of Germany ....... 3743142

[51] Int. Cl.$^5$ .................... C08F 263/04; C08F 255/02
[52] U.S. Cl. ..................... 525/267; 525/281; 525/291; 525/302; 525/324; 525/308; 525/317; 524/535; 524/817

[58] Field of Search .......... 525/267, 281, 291; 524/535, 817

[56] References Cited

U.S. PATENT DOCUMENTS 3,856,733 12/1974 Sturt et al. ............... 525/302
4,246,387 1/1981 Deutsch ................... 525/303

Primary Examiner—Ana L. Carrillo
Assistant Examiner—Vasu S. Jagannathan
Attorney, Agent, or Firm—Burgess, Ryan and Wayne

[57] ABSTRACT

A process is provided for the production of a graft copolymer by means of emulsion polymerization. The graft base used is a sulfonate group-containing vinyl ester/ethylene latex which is stabilized exclusively by an anionic emulsifier (CMC$\geq$0.5% by weight in $H_2O$) and is grafted, preferably with vinyl chloride, without further addition of emulsifier or protective colloid. The graft copolymers according to the invention have good water resistance and very good thermoplastic processability. They are useful as impact modifiers and for the production of articles, such as, soft to semi-hard moldings.

21 Claims, No Drawings

PROCESS FOR EMULSION POLYMERIZATION OF GRAFT COPOLYMERS

CROSS-REFERENCE TO RELATED APPLICATIONS

This application is a continuation-in-part of U.S. Ser. No. 254,368, filed Oct. 5, 1988 abandoned.

BACKGROUND OF THE INVENTION

1. Field of the Invention

The invention relates to a process for emulsion polymerization of graft copolymers using a sulfonate group-containing, optionally crosslinked vinyl ester/ethylene copolymer as the graft base and grafting on one or more monomers other than ethylene and vinyl esters. The invention also relates to articles comprised of at least one thermoplastic polymer and the graft copolymer prepared by the process.

2. Description of the Related Art

A number of processes for graft copolymerization have been described. In DE-A 1,495,694 (U.S. Pat. No. 3,358,054), a process is claimed in which a vinyl acetate/ethylene (VAE) copolymer is employed in the solid state. The solid VAE copolymer is dissolved in the vinyl chloride monomer phase, dispersed in water and grafted using a suspension polymerization process. The time-consuming and expensive dissolution of the solid resin is disadvantageous in this process. Due to the rapidly increasing viscosity of the solution, it is difficult to achieve solid resin contents of greater than 15%. Due to the relatively large particle size which is associated with the suspension polymerization process, inhomogenity with respect to the copolymer composition can occur at short solution times.

In the process of DE-A 2,344,553 (U.S. Pat. No. 4,006,201), the graft base initially introduced is an aqueous vinyl acetate/ethylene dispersion. Vinyl chloride is metered in during the graft copolymerization. The production of the VAE dispersion and the grafting take place in the presence of a nonionic emulsifier and protective colloid. The product is produced with the consistency of suspension PVC. Using this procedure, a reduction in the reaction time is achieved due to the use of the VAE dispersion. However, the use of a H$_2$O-soluble protective colloid and a nonionic emulsifier has a deleterious effect. If a protective colloid is employed to stabilize the dispersion used as the graft base, products having high water sensitivity result. Due to the incompatibility of the protective colloid and graft copolymer, turbid molding compositions are obtained when the graft copolymers are processed. Nonionic emulsifiers, in particular ethylene oxide condensation products which are usually employed for stabilization of dispersions, result in thermal instability during thermoplastic processing of VC-grafted VAE copolymers; the products tend to discolor.

DE-A 2,104,870 (U.S. Pat. No. 3,856,733) describes the grafting of a vinyl acetate/ethylene copolymer latex with vinyl chloride under emulsion polymerization conditions. In this case, further emulsifier, specifically nonionic ethylene oxide condensates and a protective colloid, are added during the graft copolymerization in addition to the emulsifier and protective colloid present in the latex. Although inhomogeneities of the graft product are thus avoided due to the smaller particle sizes in the emulsion process, the above-described adverse effects with respect to processability and product quality again occur here due to the use of relatively large amounts of nonionic emulsifier and protective colloid.

The object of the invention is to provide a process for the production of graft copolymers, and articles prepared therefrom, in which a vinyl ester/ethylene latex is grafted, preferably with vinyl chloride, using the emulsion polymerization process without the above-described disadvantages with respect to processability and product quality occurring.

SUMMARY OF THE INVENTION

It has been discovered that, by introducing sulfonate group-containing comonomers into the vinyl ester-/ethylene copolymer, stable latices are obtained, by use of small amounts of anionic emulsifier and omission of a protective colloid. In the subsequent grafting step, no additional emulsifier or protective colloid is required to stabilize the graft copolymer latex.

The invention relates to a process for the production of graft copolymers by grafting a vinyl ester/ethylene copolymer, preferably a vinyl acetate/ethylene copolymer, which has been initially introduced as an aqueous latex with one or more monomers, other than vinyl ester and ethylene, in the aqueous phase, wherein (I) the vinyl ester/ethylene copolymer contains:
 a) about 35-60% by weight of ethylene,
 b) about 40-65% by weight of a vinyl ester of branched or unbranched carboxylic acids having about 1 to about 12 carbon atoms,
 c) about 0.05-1.0% by weight of at least one ethylenically mono-unsaturated monomer containing sulfonate groups, and
 d) about 0-2.0% by weight of ethylenically polyunsaturated, crosslinkable monomers.

(II) the graft copolymers are produced by emulsion polymerization at 30°-90° C. and at ethylene pressures of from about 40 to about 90 bar abs. using about 0.05-1.5% by weight, relative to the comonomer phase, of an anionic emulsifier having a critical micelle concentration (CMC) $\geq$0.5% by weight in water using water-soluble free-radical initiators, if appropriate in the presence of a redox initiator system, and (III) the latex is grafted at about 30°-90° C., without addition of further emulsifiers or protective colloids, with one or more monomers, other than a vinyl ester and ethylene, whose homopolymers have glass transition temperatures $\geq$50° C.

DESCRIPTION OF THE PREFERRED EMBODIMENTS

The vinyl ester/ethylene graft base preferably contains a) about 40-50% by weight of ethylene, b) about 50-60% by weight of a vinyl ester, and c) about 0.1-0.5% by weight of ethylenically mono-unsaturated monomers containing sulfonate groups. The particularly preferred graft bases are vinyl acetate/ethylene copolymers containing sulfonate groups. Vinyl acetate, vinyl propionate, vinyl isobutyrate, vinyl versatate, or vinyl laurate, preferably vinyl acetate, can be employed, as component b).

The sulfonate-containing comonomers employed are alkali metal salts or ammonium salts of vinyl sulfonate or salts of sulfoalkyl esters of (meth) acrylic acid or salts of sulfoalkylamides of (meth) acrylic acid. These compounds are preferably employed as alkali metal salts. The potassium salts of vinyl sulfonate and of 2-acrylamido-2-methylpropanesulfonic acid are particularly preferred.

Examples of comonomers of group d), which are preferably present in the graft base to the extent of about 0.01 to 0.5% by weight, are vinyl and allyl esters of unsaturated $C_3$ to $C_8$-monocarboxylic acids, mono- or divinyl and diallyl esters of saturated or unsaturated $C_4$ to $C_{10}$-dicarboxylic acids, and also triallyl cyanurate and allyl ethers of polyfunctional alcohols. Divinyl adipate and triallyl cyanurate are preferably employed.

The vinyl ester/ethylene graft base is produced by emulsion polymerization at a temperature from about 30° to 90° C. and at ethylene pressures from 40–90 bar abs. in the presence of an anionic emulsifier having a critical micelle concentration (CMC) $\geq 0.5\%$ by weight in water. Anionic emulsifiers having a CMC $>1\%$ by weight in water are preferably employed. Examples of useful emulsifiers are lower sulfosuccinates such as the commercially available diisohexyl ester Aerosol MA (CMC 1.6%) of American Cyanamid, Rewopol SBMB 80 (CMC 1.5%) from Rewo, Steinau, or diamyl sulfosuccinates such as Aerosol AY 100 (CMC 2.2%), or dibutyl sulfosuccinates (CMC 3.0%). The anionic emulsifiers can be employed alone or as mixtures in an amount from about 0.05 to about 1.5% by weight, relative to the total weight of the comonomer phase.

The polymerization is started with initiation by means of customary water-soluble free-radical formers such as alkali metal salts of persulfates, hydroperoxides (hydrogen peroxide, tertiarybutyl hydroperoxide) and perphosphates. Potassium persulfate is preferably employed. In the case of thermal initiation, the reaction is preferably carried out at about 70° to 90° C. Activation of the free-radical formers by means of reducing agents such as, for example, sulfites or sulfinic acid derivatives, is particularly preferred. In this case, the polymerization is carried out at a temperature between about 30° and about 55° C. The total amount of initiators employed is preferably a maximum of about 1.0% by weight, relative to the total weight of the comonomer phase.

The ethylene pressure is set at the beginning of the polymerization and preferably kept constant by reinjection. The addition of comonomers b), c) and d) can be accomplished in any desired manner. Comonomer b), vinyl acetate is preferably initially introduced in an amount of about 5 to about 20% by weight, and the remainder is metered in during the course of the polymerization. Comonomers c) and d) can be metered into the polymerization zone in their entirety during the polymerization, or partially introduced at the beginning of the polymerization and the remainder metered into the polymerization zone during the polymerization. When sulfonate group-containing acrylic acid derivatives are used, the entire amount is preferably metered into the polymerization zone during the polymerization.

The components of the initiator system are preferably metered into the polymerization zone during the polymerization. The addition of the emulsifier can take place in any desired manner; preferably, part of the emulsifier is initially introduced and the remainder is metered into the polymerization zone during the polymerization.

The solids content of the vinyl ester/ethylene copolymer latex is preferably about 30 to about 60% by weight.

The graft monomers used in the process are vinyl monomers whose homopolymers have glass transition temperatures $\geq 50°$ C. such as, for example, styrene, vinyl toluene, methyl (meth)acrylate or vinyl chloride, or mixtures of these monomers. In a preferred embodiment, vinyl chloride is grafted onto the vinyl ester/ethylene copolymer. The amount of graft monomer added to the polymerization zone is set so that the final graft product contains between about 30 and about 95% by weight of these monomer units.

For the graft copolymerization, the vinyl ester/ethylene latex is initially introduced into the polymerization zone. The graft monomer phase can be introduced initially or metered into the polymerization zone during the course of the polymerization. Preferably up to about 50% by weight of the graft monomer phase is initially introduced into the polymerization zone and the rest is metered in during the polymerization. In addition, water is initially introduced in an amount such that grafting results in a latex having a solids content of about 30 to 60%.

The initiators are known free-radical formers; water-soluble free-radical formers such as potassium persulfate, hydrogen peroxide or hydroperoxides, are preferably employed. Reducing agents can also be employed with the initiators. The total amount of initiators employed is preferably up to about 1.0% by weight relative to the total amount of graft monomer. The graft copolymerization preferably takes place without further addition of protective colloid or emulsifier.

The grafting is carried out at a temperature between about 30° and about 90° C., in accordance with the K value desired for the final product. In the case of grafting of vinyl chloride, the vinyl chloride is metered into the polymerization zone at a rate such that the pressure in the polymerization reactor remains below the saturation pressure.

The graft copolymer latex is worked up by spray drying, roll drying or by coagulation with subsequent drying, preferably by spray drying. At a low VC content (less than about 45% by weight of VC) in the graft copolymer, anti-blocking agents are added during the spray drying.

As previously indicated, the present invention is also directed to articles comprised of at least one thermoplastic polymer and the graft copolymers prepared in accordance with the process of the invention.

The graft copolymers which can be produced by the process of the invention are, therefore, suitable as impact modifiers in blends with PVC or as additives in polymer alloys. Because of the low emulsifier content, the graft copolymers of the invention have good water resistance and high thermal stability. They are, therefore, suitable for thermoplastic processing for the production of articles, such as flexible or soft moldings, and, in particular, sheet-like structures and moldings.

For the production of articles with high impact resistance, 5 to 80% by weight of the graft polymer are mixed with 95 to 20% by weight of a thermoplastic polymer, e.g., PVC, together with conventional additives such as stabilizers, fillers, lubricants or pigments in the amounts known to those skilled in this art. The moulding process optionally can be carried out in high-speed mixers, single-screw extruders, roll mills, or in mixing mills. The impact-resistant articles can be processed from the powdered or preplastificated mixtures in extruders, injection moulding machines, or for the production of sheet-like articles in calenders.

The examples below serve to further illustrate the invention:

EXAMPLE 1

A dispersion of a vinyl acetate/ethylene copolymer (VAc/E) was produced in a stirred autoclave at 40° C. under an ethylene pressure of 65 bar. In this procedure, 1/10 of the vinyl acetate was present in the polymerization vessel and the remainder was metered in during 8 hours after initiation of the polymerization; the reaction was then continued for a further 3 hours, with the ethylene pressure maintained at 65 bar for an additional 1.5 hours. The emulsifier comprised 1.03% by weight relative to VAc/E, of a diisohexyl sulfosuccinate (Aerosol MA from American Cyanamid), which was divided in the ratio 1:4 between amounts initially in the vessel and the amount added during the polymerization. An amount of 0.26%, relative to VAc/E, of the K salt of 2-acrylamido-2-methylpropanesulfonic acid was metered in during the polymerization. The crosslinking component was 0.12% by weight relative to VAc/E, of divinyl adipate, which was divided in the ratio of 1:50 between the amount initially present in the polymerization vessel and the amount metered in. The reaction was controlled in a customary manner by adding 0.48% of potassium peroxodisulfate and 0.11% of sodium formaldehyde sulfoxylate, in each case relative to VAc/E, over the course of the polymerization. The dispersion was adjusted to a pH of 5.5 using KOH solution. The resultant VAc/E dispersion had a solids content of 40.4% and contained 45% of ethylene incorporated into the polymer; the particle diameter was 268 nm (measured using Nanosizer ®).

COMPARISON EXAMPLE 1

Example 1 was repeated except that, instead of the 0.26% relative to VAc/E K salt of 2-acrylamido-2-methylpropanesulfonic acid, 0.56% of acrylic acid, relative to VAc/E, was metered in to the polymerization vessel during the polymerization. In order to achieve stability on pressure release, it was necessary to adjust the pH of the dispersion to 7. The ethylene content of the polymer was 42.3% and the particle size of the dispersion was 238 nm.

COMPARISON EXAMPLE 2

The procedure of Example 1 was repeated except that the diisohexyl sulfosuccinate was replaced by a nonionic emulsifier (isotridecanol containing 15 condensed ethylene oxide units). The ethylene content of the polymer was 45% and the particle size of the dispersion was 660 nm.

GRAFT EXAMPLES 1 to 3

The VAc/E copolymer dispersions of Example 1 and Comparison Examples 1 and 2 were each initially introduced into a stirred autoclave and diluted with water to a solids content of 27%. An amount of 0.03%, relative to the weight of VAc/E, of Na sulfite and 31.5%, relative to the weight of VAc/E, of vinyl chloride were initially introduced into the autoclave. The mixture was heated to 58° C. and the polymerization was initiated by metering into the autoclave a 0.5% strength K peroxodisulfate solution. After commencement of the polymerization, a further 73.5%, relative to VAc/E, of vinyl chloride was metered into the autoclave over the course of 8 hours. The reaction was maintained by further addition of the 0.5% strength K peroxodisulfate solution. The conversion of the vinyl chloride was 96%.

In order to test the product quality and processability, the resultant dispersions were dried and, with addition of the additives which are customary in PVC technology processed in a bench roll mill at 180° C. The assessment of the films obtained is summarized in Table 1. The superior properties of the product according to the invention, of Graft Example 1 (grafting of the latex from Example 1), are clearly shown. In contrast, the graft copolymers produced from grafting of the latexes from Comparison Examples 1 and 2 and the product according to U.S. Pat. No. 4,006,201 clearly exhibit inferior properties with respect to surface quality, heat stability and processability.

TABLE 1

Assessment of Calendered Films of Grafts Polymers

| Product Made From Grafting of | Appearance | Surface | Rolling Stability* At 180° C. (min.) | Processability |
|---|---|---|---|---|
| Example 1 | Colorless, transparent | Smooth, Homogeneous | 45 | Very Good |
| Comparison Example 1 | Yellowish, transparent | Rough, Inhomogeneous | 15 | Poor |
| Comparison Example 2 | Brown, Transparent | Smooth, Homogeneous | 20 | Moderate |
| According to U.S. Pat. No. 4,006,201 | Yellowish, Turbid | Rough, Inhomogeneous | — | Good |

*Minutes before discoloration

What is claimed is:

1. A process for the production of graft copolymers which comprises forming a vinyl ester/ethylene emulsion copolymer containing, in copolymerized form:
   a) from about 35–about 60% by weight of ethylene,
   b) from about 40–about 65% by weight of at least one vinyl ester of a carboxylic acid having from 1 to about 12 carbon atoms,
   c) from about 0.05 to about 1.0% by weight of at least one ethylenically unsaturated monomer containing sulfonate groups selected from the group consisting of salts of vinyl sulfonic acid, salts of sulfoalkyl ester of (meth)acrylic acid and sulfoalkylamides of (meth)acrylic acid, and
   d) about 0 to about 0.5% by weight of at least one ethylenically polyunsaturated, crosslinkable monomer by emulsion polymerization of a mixture of monomers at a temperature of from about 30° C. to about 90° C. at an ethylene pressure of from about 40 to 90 bar in the presence of from about 0.05 to about 1.5% by weight, relative to the amount of comonomers, of an anionic emulsifier having a critical micelle concentration greater than about 0.5% by weight in water, and a water-soluble free radical initiator without the addition of other emulsifiers and protective colloids; and grafting to the vinyl ester/ethylene copolymer emulsion, at a temperature in the range of from about 30° C. to about 90° C., without the further addition of emulsifiers or protective colloids, at least one monomer other than a vinyl ester and ethylene, whose homopolymers have a glass transition temperature about 50° C.

2. A process of claim 1, wherein the vinyl ester is vinyl acetate.

3. A process of claim 2, wherein the anionic emulsifier has a critical micelle concentration greater than about 1.0% by weight in water.

4. A process of claim 2, wherein the ethylenically unsaturated monomer containing sulfonate groups is a salt of 2-acrylamido-2-methylpropanesulfonic acid.

5. The process of claim 2, wherein the sulfur containing composition comprises a salt of 2-acrylamido-2-methylpropanesulfonic acid.

6. A process of claim 2, wherein component d) comprises from about 0.01 to about 0.5% by weight of at least one monomer selected from the group consisting of divinyl adipate and triallyl cyanurate.

7. A process of claim 1, wherein the anionic emulsifier has a critical micelle concentration greater than about 1.0% by weight in water.

8. A process of claim 7, wherein component d) comprises from about 0.01 to about 0.5% by weight of at least one monomer selected from the group consisting of divinyl adipate and triallyl cyanurate.

9. A process of claim 8, wherein the ethylenically unsaturated monomer containing sulfonate groups comprises an alkali metal salt of a sulfonate group-containing monomer.

10. A process of claim 9, wherein the graft monomer is vinyl chloride.

11. A graft copolymer of the process of claim 10.

12. A process of claim 1, wherein the ethylenically unsaturated monomer containing sulfonate groups is a salt of vinyl sulfonic acid.

13. The process of claim 1, wherein the ethylenically unsaturated monomer containing sulfonate groups is a salt of 2-acrylamido-2-methylpropanesulfonic acid.

14. A process of claim 1, wherein component d) comprises from about 0.01 to about 0.5% by weight of at least one monomer selected from the group consisting of divinyl adipate and triallyl cyanurate.

15. A process of claim 1, wherein the ethylenically unsaturated monomer containing sulfonate groups comprises an alkali metal salt of a sulfonate group-containing monomer.

16. A process of claim 1, wherein the graft monomer is vinyl chloride.

17. An article comprising at least one thermoplastic polymer and an impact modifier comprising a graft copolymer of the process of claim 16.

18. A thermoplastically processable composition comprising a graft copolymer of the process of claim 16.

19. A graft copolymer of the process of claim 1.

20. An article comprising at least one thermoplastic polymer and an impact modifier comprising a graft copolymer of the process of claim 1.

21. A thermoplastically processable composition comprising a graft copolymer of the process of claim 1.

* * * * *